United States Patent
Ruohonen et al.

(10) Patent No.: US 9,999,787 B1
(45) Date of Patent: Jun. 19, 2018

(54) BEAM LIMITING DEVICE FOR INTENSITY MODULATED PROTON THERAPY

(71) Applicant: Varian Medical Systems International AG, Cham (CH)

(72) Inventors: Jarmo Ruohonen, Vantaa (FI); Sami P. Siljamaki, Helsinki (FI)

(73) Assignee: Varian Medical Systems International AG., Cham (CH)

( * ) Notice: Subject to any disclaimer, the term of this patent is extended or adjusted under 35 U.S.C. 154(b) by 0 days. days.

(21) Appl. No.: 15/453,221

(22) Filed: Mar. 8, 2017

(51) Int. Cl.
*A61N 5/00* (2006.01)
*A61N 5/10* (2006.01)

(52) U.S. Cl.
CPC ......... *A61N 5/1047* (2013.01); *A61N 5/1043* (2013.01); *A61N 5/1081* (2013.01); *A61N 2005/1087* (2013.01); *A61N 2005/1094* (2013.01); *A61N 2005/1095* (2013.01)

(58) Field of Classification Search
CPC .. A61N 5/1047; A61N 5/1043; A61N 5/1081; A61N 2005/1087; A61N 2005/1094; A61N 2005/1095
USPC ........................................... 250/492.1–492.3
See application file for complete search history.

(56) References Cited

U.S. PATENT DOCUMENTS

| | | | | |
|---|---|---|---|---|
| 5,818,902 A * | 10/1998 | Yu | ......... | A61N 5/1047 378/151 |
| 2005/0029471 A1* | 2/2005 | Kraft | ......... | G21K 1/04 250/492.1 |
| 2006/0017015 A1* | 1/2006 | Sliski | ......... | G21K 1/08 250/492.3 |
| 2010/0046713 A1* | 2/2010 | Nord | ......... | A61N 5/1042 378/125 |
| 2010/0237259 A1* | 9/2010 | Wang | ......... | A61N 5/1049 250/492.1 |
| 2011/0105821 A1* | 5/2011 | Dieter | ......... | A61N 5/1043 600/1 |
| 2011/0317895 A1* | 12/2011 | Poludniowski | ...... | A61N 5/1047 382/131 |
| 2014/0330065 A1* | 11/2014 | Vilsmeier | ......... | A61N 5/1045 600/1 |
| 2017/0087386 A1* | 3/2017 | Mellenberg | ......... | A61N 5/1045 |

* cited by examiner

*Primary Examiner* — Michael Maskell

(57) ABSTRACT

To overcome the difficulties inherent in conventional proton therapy systems, new techniques are described herein for synchronizing the application of proton radiation with the periodic movement of a target area. In an embodiment, a method is provided that combines multiple rescans of a spot scanning proton beam while monitoring the periodic motion of the target area, and aligning the applications of the proton beam with parameters of the periodic motion. For example, the direction(s) and frequency of the periodic motion may be monitored, and the timing, dose rate, and/or scanning direction and spot sequence of the beam can be adjusted to align with phases in the periodic motion.

20 Claims, 6 Drawing Sheets

300

300

Exemplary Computer System 600

BEAM LIMITING DEVICE FOR INTENSITY MODULATED PROTON THERAPY

TECHNICAL FIELD

Embodiments of this invention relate generally to directed irradiated particle beam applications. More specifically, embodiments of this invention are directed to improved methods and systems for limiting a beam of irradiated particles to achieve a target dosage.

BACKGROUND OF THE INVENTION

Proton therapy is a type of external beam radiation therapy that is characterized by the use of a beam of protons to irradiate diseased tissue. A chief advantage of proton therapy over other conventional therapies such as X-ray or neutron radiation therapies is that proton radiation can be limited by depth, and therefore the exposure to inadvertent radiation can be avoided or at least limited by non-target cells having a depth beyond a target calculated area.

A popular implementation of proton therapy uses monoenergetic pencil beams at varying energy levels, which are spot-scanned over a target area for one or more layers of depth. By superposition of several proton beams of different energies, a Bragg peak can be spread out to cover target volumes using a uniform, prescribed dose. This enables proton radiation applications to more precisely localize the radiation dosage relative to other types of external beam radiotherapy. During proton therapy treatment, a particle accelerator such as a cyclotron or synchrotron is used to generate a beam of protons from, for example, an internal ion source located in the center of the particle accelerator. The protons in the beam are accelerated (via a generated electric field), and the beam of accelerated protons is subsequently "extracted" and magnetically directed through a series of interconnecting tubes (called a beamline), often through multiple chambers, rooms, or even floors of a building, before finally being applied through a radiation application device at an end section of beam line (often through a radiation nozzle) to a target volume in a treatment room.

As the volumes (e.g., organs, or regions of a body) targeted for radiation therapy are often below the surface of the skin and/or extend in three dimensions, and since proton therapy—like all radiation therapies—can be harmful to intervening tissue located in a subject between the target area and the beam emitter, the precise calculation and application of correct dosage amounts and positions are critical to avoid exposing regions in the radiation subject outside the specific areas targeted to receive radiation.

As a solution to this issue, radiation devices have been equipped with specialized computer-controlled hardware collimator devices, such as collimator jaws and multi-leaf collimators (MLCs), which control the shape and size of a beam application field. These devices have been developed to deliver fields conforming to the projection of the target with greater ease and accuracy. In more advanced applications, the collimator jaws and/or the individual leaves of an MLC are moved separately under computerized control systems at desired speeds during periods of radiation (e.g., beam-on). This has enabled the generation of spatially modulated radiation fields, since each leaf attenuates the beam for a different time period. The resulting intensity modulated proton therapy (IMPT) has allowed the application of high dose volumes that conform more closely to the shape of complicated targets.

However, while these developments allow programming of more accurate beam fields, the devices themselves are still subject to mechanical errors or measurement variances that may result in inaccuracies during radiation application. More generally, the devices were originally developed for photon radiation applications, which used a broader starting particle beam. The development of thin, spot-scanning pencil proton beams obviate much of the need for complicated beam field shaping components, which can be less optimized and cost-efficient to use. This is especially true for modern MLCs that can have tens of leaves and corresponding motors, making them extremely costly to manufacture and maintain, and complex. Moreover, typical jaw and MLC shapes are implemented with angularly shaped components (e.g., rectangular blocks and/or leaves) which can be ineffective to shape a beam field optimally to treat target areas with less sharp angles.

Another conventional solution involves using block apertures of a rigid material, shaped specifically to limit beam fields to a particular target area and for a particular radiation subject. Since these apertures are customized for each application, the time required to plan, produce, and install these devices can be extensive, and may not be suitable for time-sensitive applications. Moreover, use of subject and tumor-specific apertures require manual effort to change and swap out apertures in lieu of other apertures during beam applications at different depths or orientations, which can be time and user-intensive.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in conventional beam limiting techniques for proton therapy systems, new techniques are described herein for accurately and cost-effectively shaping proton beam fields according to radiation plans. In an embodiment, a device is provided that can be positioned within the beam line in a radiation nozzle to shape an emitted beam field by shielding areas outside of the target area from receiving inadvertent radiation. In one or more embodiments, the beam limiting structure can be rotated so that an aperture in the structure or device can be aligned with a perimeter of a target area in a subject.

In one or more embodiments, alignment of the beam limiting structure with a perimeter of a target area and a beam application can be implemented with a control system operable to control a position of the beam limiting device or structure using as little as one motor per dimension (e.g., x and y). Via control signals issued from the control system (and configured based on a radiation application plan, for example) a beam limiting structure can be rotated and re-positioned to re-align with a perimeter of a single spot-scan application for each of a set of spot applications.

In one or more embodiments, the beam limiting structure could be made of a dense shielding material, such as tungsten or brass, and approximate a circular shape such as a ring or spiral, with an interior diameter that is significantly larger than the diameter of a spot application. The structure can be moved to limit the size and shape of the spot from any direction, essentially creating a sharp penumbra (i.e., a step-like field edge) and allowing significant conformance to a target shape. In one or more embodiments, the interior diameter of the beam limiting structure may be implemented as an aperture. In alternate embodiments, a portion of all of the interior area can be made of a lighter material such as plastic. According to one or more embodiments, the beam limiting structure or device can be moved along with the spot location, e.g., as the nozzle itself is re-positioned or rotated (by a moveable gantry, for example), by using the control system to position and rotate the structure to align the shielding section to the correct location at each spot application.

According to further embodiments, the specific size, shape, and even material of the beam limiting structure can have a wide range, and optimized particular for different uses or beam energies, or even to provide the sharpest possible delineation of radiation. In one or more embodiments, the beam limiting structure can even be used to delineate spots that are not located along an outer edge of a target area, and the outer diameter of the beam limiting structure can be used to fit concavities in a target area. Various shapes of the beam limiting structure can be used for additional purposes. For example, for beam limiting structures that are spiral-shaped, a continuum of curvatures can be obtained using both the inner and outer diameters. By rotating and moving the shape, the shielding portion can be accurately matched with the intended border shape. In addition to curvatures, the beam limiting structure can also contain, for example, straight segments and corners for even greater versatility.

In still further embodiments, additional mechanisms may be used to tilt the beam limiting structure or device away from the plane perpendicular to the beam axis. According to such embodiments, the perimeter of the beam limiting device or structure can be matched to the beam divergence, thereby minimizing disadvantageous scattering from the aperture. Due to the novel shape of the beam limiting structures proposed herein, scattering effects of proton beam applications can be modeled and shaped simply and robustly compared to conventional implementations such as MLCs and arbitrarily shaped block apertures.

According to another embodiment, a method is provided that is operable to perform beam field shaping using a beam limiting structure or device in a radiation nozzle. In an embodiment, the method includes receiving a beam of protons from a radiation source (such as a cyclotron or synchrotron), determining a position of a target area in an application subject (based, for example, on a radiation application plan), positioning the beam limiting structure or device to obstruct a path of a proton beam and to align the beam limiting structure or device with a spot-scan application, and directing the beam of protons to the target area with the beam field modified due to the position of the beam limiting structure. In one or more embodiments, the position of the beam limiting structure and the position and orientation of the radiation nozzle itself can be dynamically aligned with the position of spot applications in the target area.

The application of irradiated particles (such as protons) can thus be directed with greater precision by aligning beam applications using a reusable, planar beam limiting device. Through the resulting modification of a beam field through the position of the beam limiting device, exposure to undesirable radiation application in non-target areas can be effectively reduced.

BRIEF DESCRIPTION OF DRAWINGS

The accompanying drawings, which are incorporated in and form a part of this specification, illustrate embodiments of the disclosure and, together with the description, serve to explain the principles of the presently claimed subject matter:

DETAILED DESCRIPTION

Figure 1:
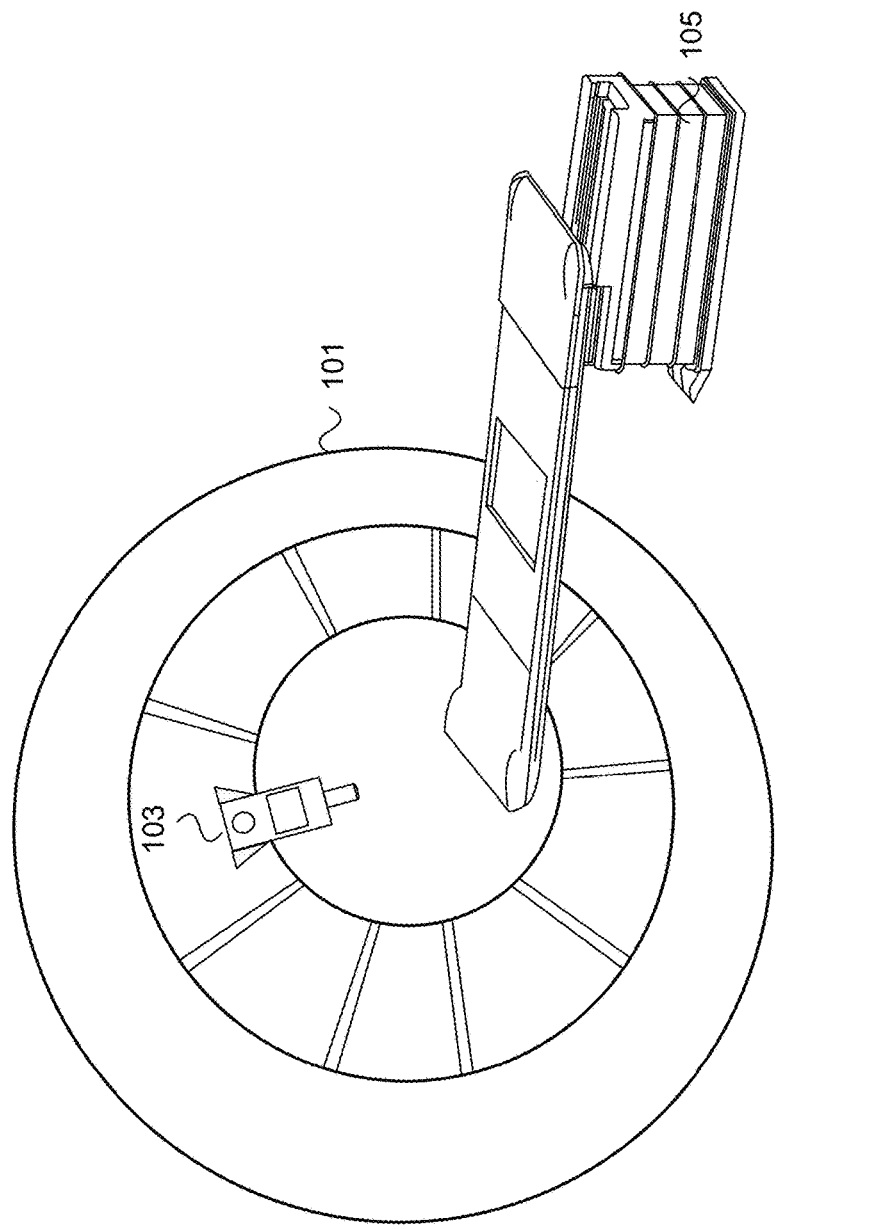
FIG. 1 depicts an exemplary proton application device, in accordance with embodiments of the present disclosure.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known processes, procedures, components, and circuits have not been described in detail as not to unnecessarily obscure aspects and features of the subject matter.

Portions of the detailed description that follow are presented and discussed in terms of a process. Although operations and sequencing thereof are disclosed in a figure herein (e.g., FIG. 5) describing the operations of this process, such operations and sequencing are exemplary. Embodiments are well suited to performing various other operations or variations of the operations recited in the flowchart of the figure herein, and in a sequence other than that depicted and described herein.

Some portions of the detailed description are presented in terms of procedures, operations, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed operation, logic block, process, etc., is here, and generally, conceived to be a self-consistent sequence of operations or instructions leading to a desired result. The operations are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While the following example configurations are shown as incorporating specific, enumerated features and elements, it is understood that such depiction is exemplary. Accordingly, embodiments are well suited to applications involving different, additional, or fewer elements, features, or arrangements.

Exemplary Radiation Application Device

FIG. 1 depicts an exemplary radiation application device 100 in a radiation application room, in accordance with various embodiments of the claimed subject matter. As presented in FIG. 1, radiation application device 100 includes a gantry 101, a radiation treatment nozzle 103, and a subject positioner 105. In one or more embodiments, the gantry 101 may comprise an opening through which at least a portion of the subject positioner 105 is able to enter (e.g., via automatic and/or mechanical means). In one or more embodiments, at least a portion of the gantry may be operable to rotate around the opening (typically while at least a portion of the subject positioner is disposed within). For example, as depicted in FIG. 1, the gantry 101 may be implemented as a ring, at least a portion of which may be rotatable around an axis bisected by the subject positioner 105.

According to one or more embodiments, the gantry 101 is configured to receive irradiated particles (such as protons) through a beam line connected to a radiation source. The radiation source may be implemented as, but is not limited to, a proton accelerator such as a cyclotron or synchrotron. In one or more embodiments, the radiation source may be positioned remotely with respect to the treatment therapy room and may be shared between multiple radiation application devices housed in multiple radiation application rooms or suites. Beam lines (e.g., vacuum sealed tubes or pipes used to convey irradiated particles) are used to connect the radiation source to each of the radiation application devices. Once received through the beam line, the irradiated particles are emitted from the radiation application device 100 through a radiation nozzle 103 connected to the gantry 101. In one or more embodiments, the radiation nozzle 103 is rotated about the opening of the gantry 101 through a rotation of at least a portion of the gantry coupled to the radiation nozzle 103. In alternate embodiments, movement of the radiation nozzle 103 may be performed via movement of one or more robotic appendages coupled to the gantry 101.

In one or more embodiments, the subject positioner 105 may include a support structure (such as a table, chair, bench, or bed) upon which a radiation subject may lie, sit, or rest upon. According to further embodiments, portions of the subject positioner 105 may be capable of movement, via automatic and/or mechanical means. For example, the incline of a portion of the resting surface may be increased or decreased (e.g., physically via a mechanism or automatically through a graphical user interface). Portions of the subject positioner 105 may also be equipped with means to rotate, extend, or retract. For example, according to one or more embodiments, a portion of the resting surface of the subject positioner 105 may be extended or physically positioned into an opening of the gantry 101, such that a radiation subject resting on the subject positioner 105 bisects the plane at which the radiation nozzle 103 is directed.

One or both of the gantry 101 and the subject positioner 105 is/are capable of maneuvering, either independently or in conjunction, to align a radiation subject positioned on the subject positioner 105 with the radiation nozzle 103. Movement of the gantry 101 and/or subject positioner 105 may include, but is not limited to, rotation, extension, retraction, contraction, adduction, abduction, etc. of one or more articulated surfaces or portions of the gantry 101, and/or subject positioner 105. In one or more embodiments, radiation nozzle 103 may also be capable of limited movement, via multi-axial rotation or extension of one or more portions, for example. Movement of the gantry 101, radiation nozzle 103, and/or subject positioner 105 may be performed automatically, via pre-programmed instructions that correspond to optimized alignments for desired iso-centers, or may be controlled remotely via a user interface.

A radiation subject may be positioned (e.g., by lying prone) on a subject positioner 105 at an initial or starting position. One or more portions of the subject positioner 105 may extend towards an opening presented by the gantry 101, such that a target area of the radiation subject is aligned with a position of the radiation nozzle 103, located on or around an inner surface of the gantry 101. In alternate or further embodiments, the gantry 101 may also rotate in an arc around the circumference of the gantry 101 to position the radiation nozzle 103 to produce the desired beam field or to do position verification of a radiation subject positioned on a subject positioner 105. Once the gantry 101, radiation nozzle 103, and/or subject positioner 105 are aligned in the desired orientation, radiation application may begin. Specifically, an iso-center in the radiation subject may be aligned with the radiation nozzle 103 via movement of the gantry 101 and/or subject positioner 105. In one or more embodiments, radiation application may comprise the application of irradiated particles generated at a (remote) particle accelerator, received in the gantry 101, and emitted (e.g., as a raster scan) as a beam field from the radiation nozzle 103 at an iso-center located in a radiation subject according to a pre-determined radiation application plan.

The radiation nozzle 103 may be configured to emit the irradiate particles in a spot scanning beam (also referred to as a "pencil beam"). In specific embodiments of the invention, system 200 is capable of three-dimensional spot scanning by using beam with varying energy levels. In one or more embodiments, the energy level for protons in the proton beam is selected based on a depth of the target and the transversal coordinates of the beam can be adjusted by the scanning system. Adjusting the energy level of the beam allows control of the depth at which the Bragg Peaks of the accelerated protons are located. The increased flexibility made available through three-dimensional spot scanning greatly improves the precision of the dose delivered to a patient so as to maximize dose delivery to a tumor and minimize damage to healthy tissue.

A spot-scanning beam may be produced by crossing two or more extracted beams at an extremely fine point in the radiation source. A target area may be irradiated with a raster scan (two-dimensional emission) of the resultant spot-scanning beam. In one or more embodiments, multiple beam fields sharing the same or proximate iso-centers may be irradiated with the spot scanning beam in a contiguous session, uninterrupted by application of the spot scanning beam to more distant or unrelated beam fields, for example. In further embodiments, beam fields may be irradiated in a contiguous beam application as an automated treatment of a set of fields without requiring the addition and/or removal of additional accessories such as (but not limited to) collimators, jaws, and range shifters, etc.

According to such embodiments, modification of the resultant beam fields may be performed by positioning a single beam limiting structure (or a beam limiting device comprising a structure and one or more motors for movement) to align the result beam field around a spot-scan in a target area. In one or more embodiments, the target area is selected according to a radiation plan, which may be stored with other radiation plans as a plurality of programmed instructions in a memory device of a controller (e.g., a computing device executing an application) of the radiation application device 100 and the emission of the beam of irradiated particles.

Exemplary Radiation Nozzle

Figure 2:
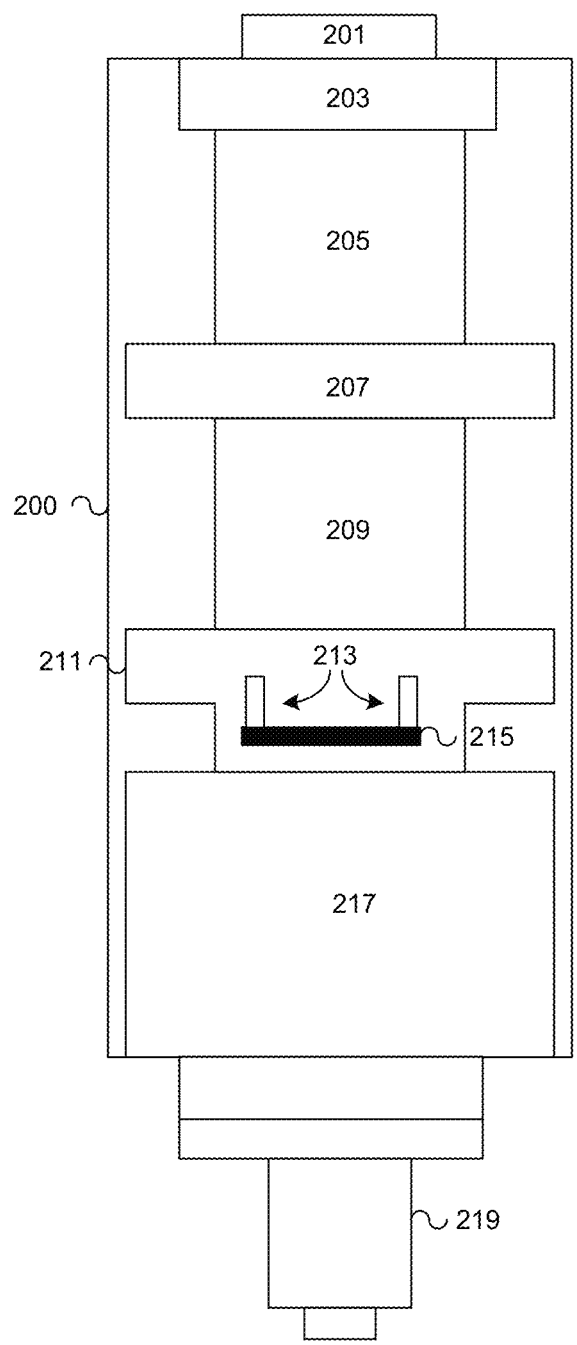
FIG. 2 depicts an exemplary radiation nozzle in a proton application device, in accordance with embodiments of the present disclosure.

FIG. 2 depicts an exemplary radiation nozzle 200 in accordance with one or more embodiments of the claimed subject matter. Radiation nozzle 200 may be implemented as, for example, the delivery system through which irradiated particles (such as protons) can be administered to a radiation subject. In one or more embodiments, the radiation nozzle 200 may be implemented to apply protons from a proton beam during a radiation treatment session of a radiation therapy plan. According to one or more embodiments, radiation nozzle 200 may be implemented as part of a beam delivery system in conjunction with a radiation application device (e.g., radiation application device 100 of FIG. 1) that includes a gantry (e.g., gantry 101 of FIG. 1), upon which the radiation nozzle 200 may be mounted.

According to one or more embodiments, the radiation nozzle 200 consists of various components used for beam shaping and beam monitoring. As depicted in FIG. 2, the radiation nozzle 200 may include one or more beam monitoring chambers (e.g., ionization chambers 201 and 217) which can detect deviations in beam position, measure a beam current, and check the beam size and uniformity. In one or more embodiments, the ionization chambers 201, 217 may be implemented using one or more electrode planes that allow the quantification of a lateral uniformity of a radiation field. In one or more embodiments, an entrance ionization chamber (e.g., ionization chamber 201) may be positioned where the extracted proton beam exits the beam line to monitor the initial size and angular distribution of the beam. One or more subsequent ionization chambers (e.g., ionization chamber 217) can be disposed further down the radiation nozzle 200 toward the radiation snout 219 to profile and measure the beam immediately before emission.

The radiation nozzle 200 may also include one or more beam shaping devices. These beam shaping devices may include, but are not limited to, beam scattering systems, correcting magnets, and beam range verifiers. Beam scattering systems (e.g., beam scattering systems 203 and 209) are used to broaden the beam and to ensure uniform, flat lateral dose profiles. Beam correcting magnets can be used to correct and align the trajectory of a beam. In one or more embodiments, beam directing magnets may be implemented as a series of magnet pairs (such as magnet pair 205 and magnet pair 207), each pair of magnets being capable of modifying the trajectory along a single axis. For example, magnet pair 205 may be used to modify the trajectory of the beam along the x-axis, whereas magnet pair 207 may be used to modify the trajectory of the beam along the y-axis. One or more beam range verifiers (not shown) may also be included in a radiation nozzle 200 verify the range of an emitted beam.

The size and shape of a beam field may be determined using various beam limiting devices. These devices may consist of, for example, collimating jaws, multi-leaf collimators, and apertures, each of which may be variably positioned to partially obstruct the beam path. According to one or more embodiments, the size and shape of a beam field may be determined by aligning a beam limiting device 211 with a perimeter of a target area and a beam application. In one or more embodiments, the beam limiting device 211 may be implemented with a beam limiting structure 215 and one or more motors 213. In one or more embodiments, the beam limiting structure 215 may be implemented as a reusable, planar structure.

In one or more embodiments, alignment of the beam limiting structure 215 with a perimeter of a target area and a beam application can be implemented with a control system operable to control a position of the beam limiting device or structure using as little as one motor per dimension (e.g., x and y). For example, the beam limiting structure 215 may be dynamically positioned within the path of the proton beam via the one or more motors. Via control signals issued from the control system (and configured based on a radiation application plan, for example) a beam limiting structure 215 can be rotated and re-positioned to re-align with a perimeter of a single spot-scan application for each of a set of spot applications. According to an embodiment, the exact number of motors 213 in the beam limiting device 211 may correspond to the number of axes of movement. For example, for movement along X and Y axes, one motor may be used to position the beam limiting structure 215 for each axis. According to still further embodiments, an additional motor may be used to tilt and/or rotate the beam limiting structure 215.

The beam limiting structure 215 may be implemented according to various shapes and sizes. For example, the beam limiting structure 215 could be made of a dense material suitable for radiation shield, such as tungsten or brass, and approximate a circular shape such as a ring or spiral, with an interior diameter that is significantly larger than the diameter of a spot application. The structure 215 can be moved to limit the size and shape of the spot from any direction, essentially creating a sharper penumbra or a step-like field edge, and allowing significant conformance to a target shape. In one or more embodiments, the interior diameter of the beam limiting structure 215 may be implemented as an aperture. In alternate embodiments, a portion of all of the interior area can be made of a lighter material such as plastic. According to one or more embodiments, the beam limiting structure 215 can be moved along with the spot location, e.g., as the nozzle itself is re-positioned or rotated (by a moveable gantry, for example), by using the control system to position and rotate the structure to align the shielding section to the correct location at each spot application.

By using the single structural component capable (via one or more motors) of being dynamically positioned in multiple axes as provided in FIG. 2, the heightened cost and complexity of having multiple collimating components (such as jaws and MLC) each with their own mechanisms for operation can be avoided. Moreover, because of the variable size and shape of the beam limiting structure 211, a beam spot can be modified to produce a multitude of beam field sizes and shapes, without having to use custom-milled apertures or require manually changing the apertures for each application or use.

Exemplary Beam Limiting Structures

Figure 3A:
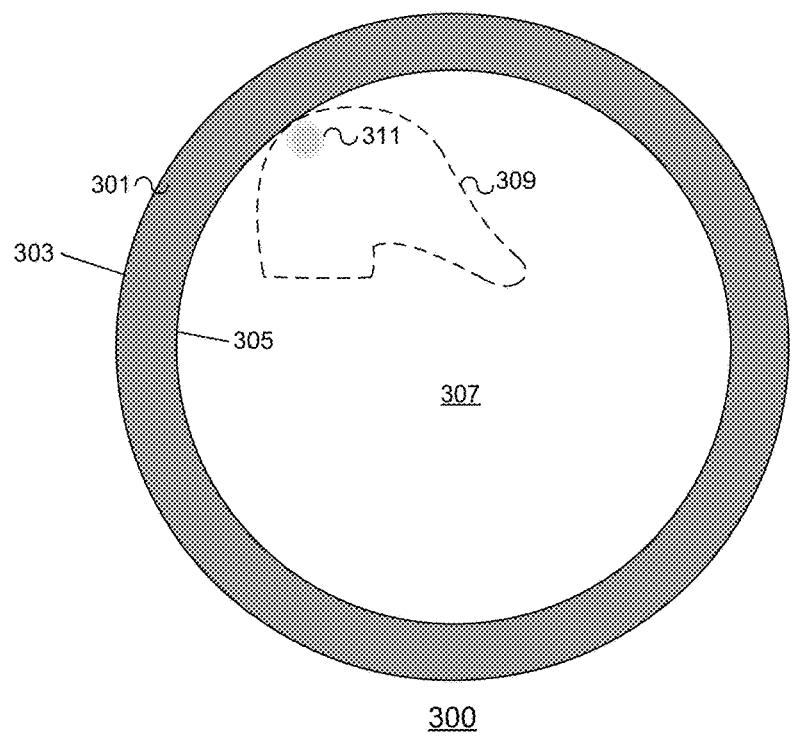
FIG. 3A depicts an exemplary beam limiting structure having a first position around a target area, in accordance with embodiments of the present disclosure.
Figure 3B:
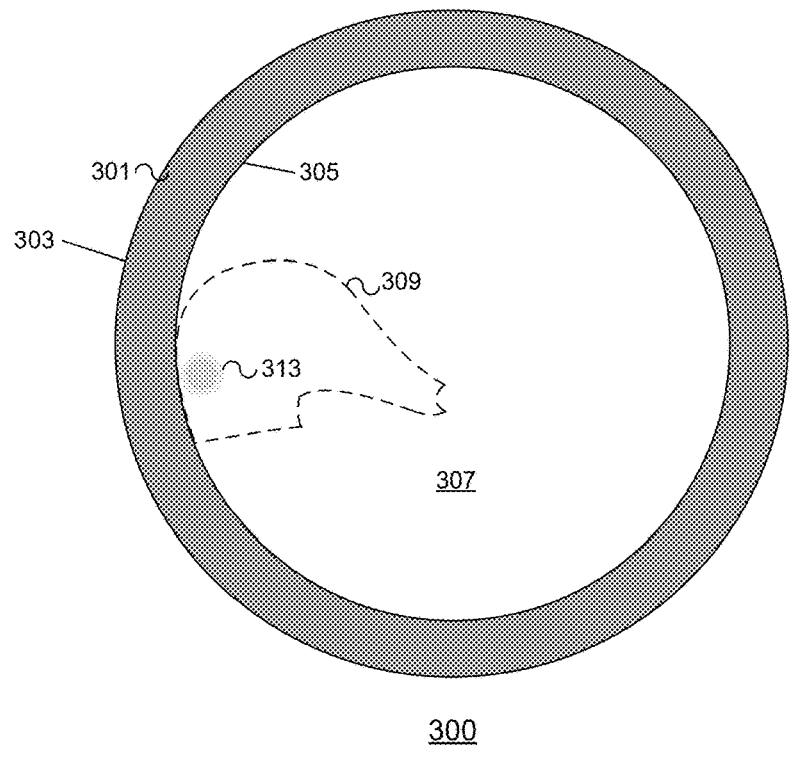
FIG. 3B depicts an exemplary beam limiting structure having a second position around a target area, in accordance with embodiments of the present disclosure.

FIGS. 3A and 3B depict an exemplary beam limiting structure 301 being positioned to align with target area (e.g., plane) 309 in a target volume, in accordance with embodiments of the present disclosure. As depicted in each of FIGS. 3A and 3B, a ring-shaped beam limiting structure 301 includes an outer diameter 303 and an inner diameter 305 enclosing an aperture 307. In one or more embodiments, a beam of irradiated particles (such as a proton beam) may be applied to the target area 309 of the target volume as a rasterized series of beam spots received over the target area as flat beam fields (e.g., beam field 311).

As presented in FIG. 3A, the beam limiting structure 301 may be positioned so as to align an arc along the inner diameter 305 around the border of the target area. The exact position of the beam limiting structure 301 may depend on the position of the beam spot. As shown in FIG. 3A for example, the beam limiting structure 301 is positioned around an upper-left border of the target area 309 so as to limit a beam spot application to a beam field 311 within the target area 309 and prevent a region outside the upper-left border of the target area 309 from receiving radiation. Similarly, as depicted in FIG. 3B, the beam limiting structure 301 is re-positioned to correspond to a new beam spot 313 in the left-center portion of the target area 309. As shown in FIG. 3B, the beam-limiting structure 301 may be re-positioned to align an arc along the left-center segment of the beam limiting structure 301 around the left border of the target area 309, thereby preventing radiation from the spot 311 to be received in tissue outside of the left border of the target area 309.

Figure 4:
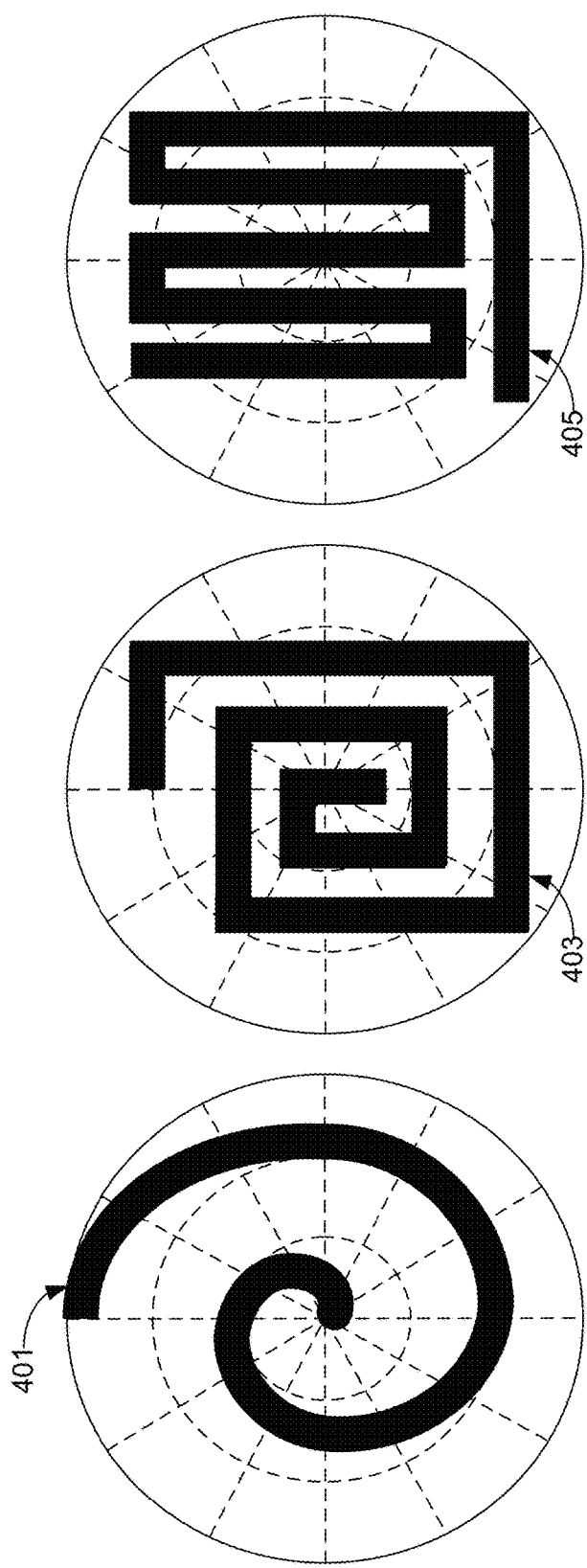
FIG. 4 depicts an alternate exemplary beam limiting structures, in accordance with embodiments of the present disclosure.

According to further embodiments, the specific size, shape, and even material of the beam limiting structure can have a wide range, and can be optimized for different uses or beam energies, or even to provide the sharpest possible delineation of radiation. For example, FIG. 4 depicts alternative exemplary beam limiting structures 401, 403, and 405, in accordance with embodiments of the present disclosure. As presented in FIG. 4, the beam limiting structure may be implemented with a curved, spiral-shape or a spiral-shaped portion or segment (e.g., beam limiting structure 401). Using the spiral-shaped beam limiting structure 401 allows a continuum of curvatures that can be used to align with variably shaped target area perimeters using both the inner and outer diameters. Alternately, the beam limiting structure may also be implemented using a concentric, right-angled shape (e.g., beam limiting structure 403). Other curved or right-angled (e.g., beam limiting structure 405) shapes may be used for the beam limiting structure that provides the ability to align with target areas by creating dose applications having a sharper penumbra or a step-like field edges.

In one or more embodiments, a beam limiting structure (e.g., beam limiting structure 215 in FIG. 2) can even be used to delineate spots that are not located along an outer edge of a target area, and the outer diameter of the beam limiting structure can be used to fit concavities in a target area. Various shapes of the beam limiting structure can be used for additional purposes. By rotating and moving the shape, the shielding portion can be accurately matched with the intended border shape. In addition to curvatures, the beam limiting structure can also contain, for example, one or more straight segments, one or more angled segments, one or more rounded segments, or any combination thereof for even greater versatility.

Positioning of Beam Limiting Structures

Figure 5:
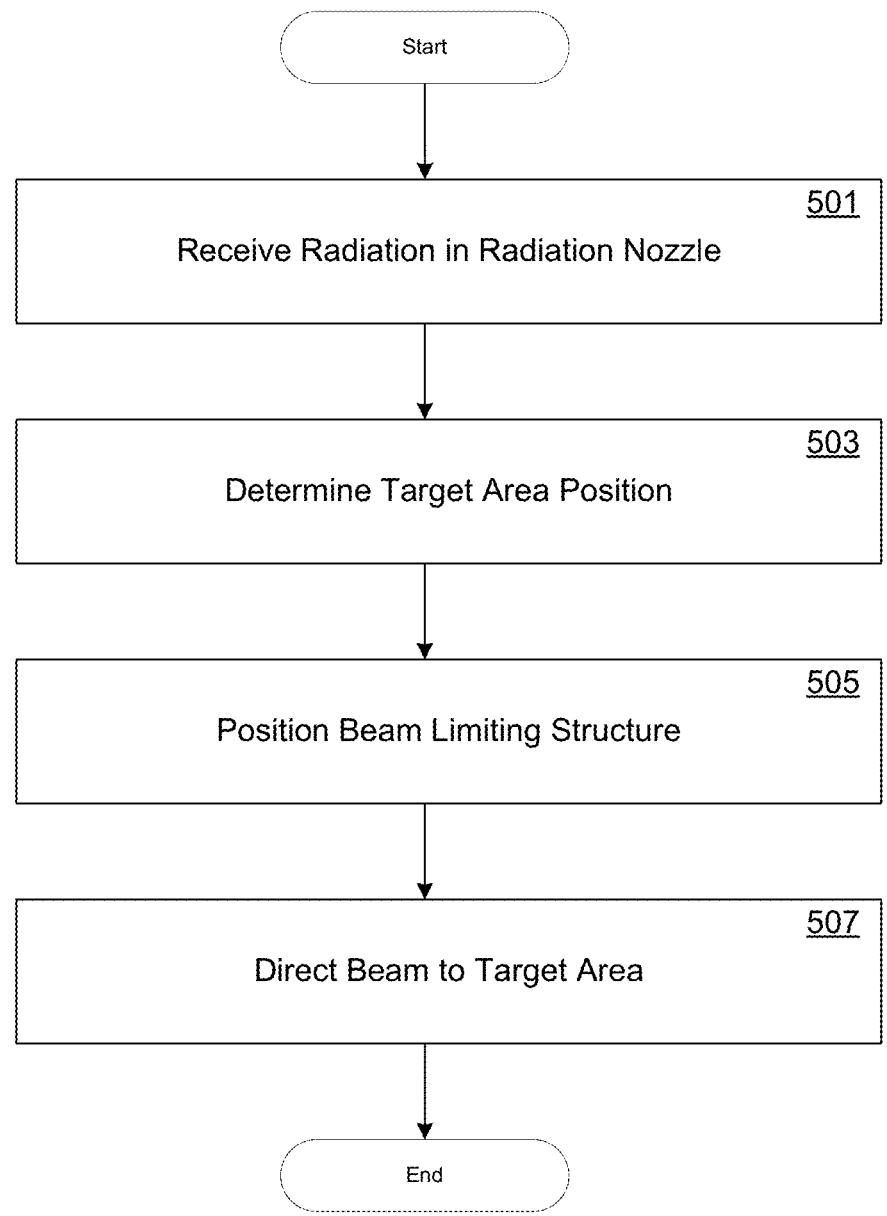
FIG. 5 depicts a flowchart of a process for aligning a radiation application session with a motion in a target area, in accordance with embodiments of the present disclosure.

FIG. 5 depicts a flow chart 500 of an exemplary process for positioning a beam-limiting structure in the radiation nozzle of a radiation application machine. Steps 501-507 describe exemplary steps comprising the process 500 depicted in FIG. 5 in accordance with the various embodiments herein described. In one embodiment, the process 500 is implemented at least in part as computer-executable instructions stored in a computer-readable medium and executed in a computing device operating to control one or more components in the radiation nozzle.

At step 501, a radiation from a radiation source is received in a radiation nozzle of a radiation application machine. In one or more embodiments, the radiation may comprise protons from a cyclotron or synchrotron, communicatively coupled to the radiation application machine (e.g., radiation therapy machine) through a beam line. In still further embodiments, the radiation nozzle may project from a moveable gantry of the radiation application machine towards a radiation subject (e.g., a radiation therapy subject), and may be configured to emit a modified beam of protons to a target area in the radiation subject according to a radiation plan. The radiation plan may comprise a proton therapy plan for a patient undergoing radiation (proton-therapy) treatment, for example. According to one or more embodiments, the radiation plan is received as data in a computing device executing an application operable to control a proton therapy treatment machine. The radiation plan may be pre-generated and associated with the radiation subject, and stored as one of a multitude of pre-generated records associated with a corresponding multitude of radiation subjects. In still further embodiments, the radiation plan may be include a timing sequence and position data for raster-scan applications of a spot-scanning proton beam during a radiation application or treatment session.

At step 503, a position of the target area is determined. The position of the target area may be determined by, for example, referencing a radiation or treatment plan for the radiation subject, that may include referencing images in a target volume of the radiation subject, performing real-time imaging and/or tracking of a target volume in the radiation subject, or a combination of any of these procedures. Once the position of the target area is determined, the position of one or more spot-scans (e.g., beam field applications) may be calculated to apply the radiation beam over the target area (e.g., as a raster scan).

At step 505, the position of a beam-limiting structure in the radiation nozzle of the radiation application machine is dynamically adjusted to modify the beam fields of the one or more spot-scans calculated at step 503. Dynamically adjusting the position of the beam-limiting structure may be accomplished by for example, calculating in a control system of a beam limiting device the optimal position, orientation, and/or rotation of the beam-limiting structure within the path of the beam in the radiation nozzle so as to shape the emitted beam-field according to the radiation plan. The positioning may be performed by one or more motors in the beam-limiting device coupled to the beam-limiting structure and controlled by the control system. In one or more embodiments, for example, a segment of the beam-limiting structure may be positioned such that the emitted beam field is aligned with a portion of a perimeter of the target area.

At step 507, the proton (e.g., spot-scanning) beam is applied according to the radiation plan determined at step 505 and emitted as one or more beam fields modified by the position of the beam-limiting structure in step 505. In one or more embodiments, the beam may be applied as a raster scan for one or more layers in a target area. In one or more embodiments, steps 503 through 507 may be performed in real-time, such that the adjustment of a radiation nozzle and/or beam-limiting structure and the application of a proton therapy beam may be aligned dynamically with the detected position of a target area.

By gating the application of the spot-scanning proton beam, and/or through alignment of the scanning position, scan direction, spot sequence and dose rate with the motion of a target area, sufficient coverage of the target area can be achieved with the target dosage without endangering neighboring tissue with misdirected or mistimed radiation.

Exemplary Computer System

Figure 6:
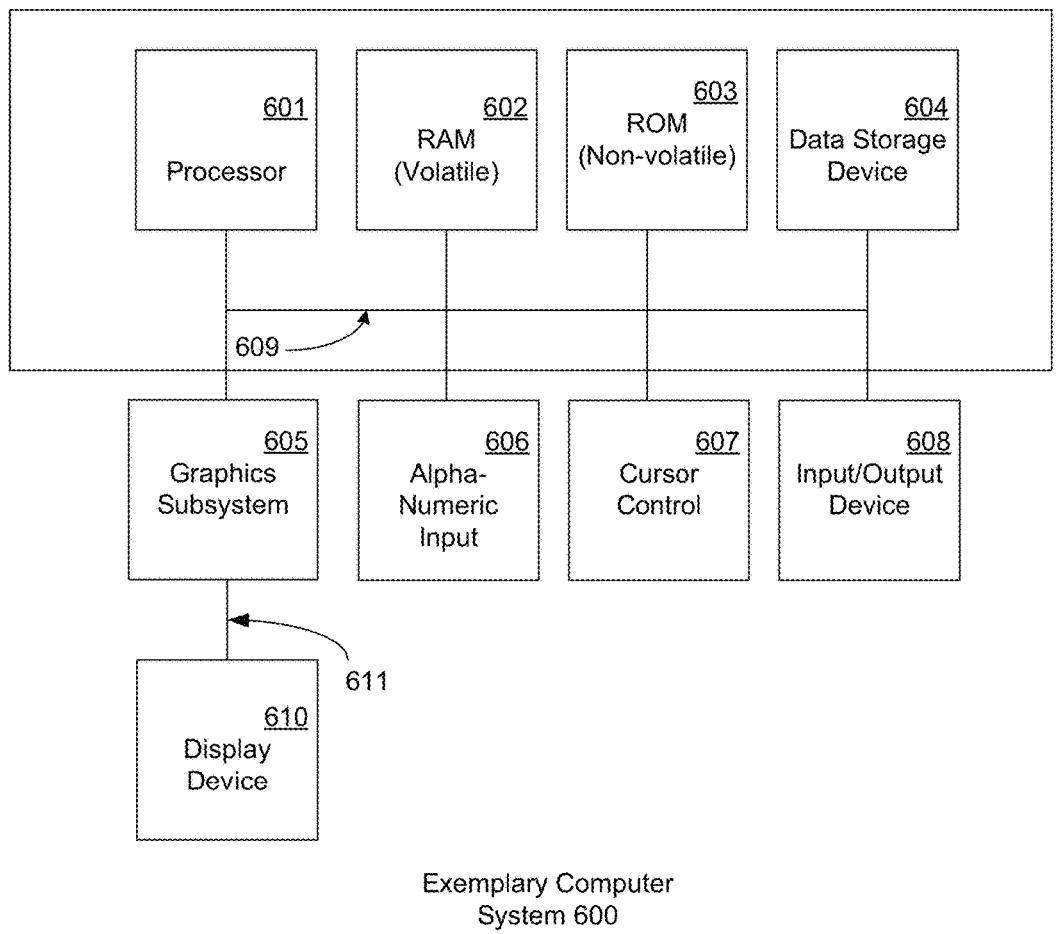
FIG. 6 depicts an exemplary computing environment, in accordance with embodiments of the present disclosure.

In one or more embodiments, alignment of the beam application with the motion of the target area may be executed as a series of programmed instructions executed on a computing environment operable to control the motion and emission of the radiation application machine described above with respect to FIG. 1. In particular, the position and alignment (e.g., rotation) of a beam limiting structure may also be controlled by a control system executing on a computing environment and implemented through one or more motors (e.g., electrical motors). FIG. 6 depicts such a computing environment, including computing system 600 upon which embodiments of the present invention may be implemented includes a general purpose computing system environment. In its most basic configuration, computing system 600 typically includes at least one processing unit 601 and memory, and an address/data bus 609 (or other interface) for communicating information. Depending on the exact configuration and type of computing system environment, memory may be volatile (such as RAM 602), non-volatile (such as ROM 603, flash memory, etc.) or some combination of the two.

The computer system 600 may also comprise an optional graphics subsystem 605 for presenting information to a radiologist, radiation administrator, or other user, e.g., by displaying information on an attached display device 610, connected by a video cable 611. According to embodiments of the present claimed invention, the graphics subsystem 605 may be coupled directly to the display device 610 through the video cable 611. A graphical user interface of an application for controlling a movement or position of a beam limiting structure may be generated in the graphics subsystem 605, for example, and displayed to the user in the display device 610. In alternate embodiments, display device 610 may be integrated into the computing system (e.g., a laptop or netbook display panel) and will not require a video cable 611.

Additionally, computing system 600 may also have additional features/functionality. For example, computing system 600 may also include additional storage (removable and/or non-removable) including, but not limited to, magnetic or optical disks or tape. Computer storage media includes volatile and nonvolatile, removable and non-removable media implemented in any method or technology for storage of information such as computer readable instructions, data structures, program modules or other data. RAM 602, ROM 603, and external data storage device (not shown) are all examples of computer storage media.

Computer system 600 also comprises an optional alphanumeric input device 606, an optional cursor control or directing device 607, and one or more signal communication interfaces (input/output devices, e.g., a network interface card) 608. Optional alphanumeric input device 606 can communicate information and command selections to central processor 601. Optional cursor control or directing device 607 is coupled to bus 609 for communicating user input information and command selections to central processor 601. Signal communication interface (input/output device) 608, also coupled to bus 609, can be a serial port. Communication interface 608 may also include wireless communication mechanisms. Using communication interface 608, computer system 600 can be communicatively coupled to other computer systems over a communication network such as the Internet or an intranet (e.g., a local area network).

In one or more embodiments, computing system 600 may be located in the same treatment room or suite as the radiation application device 100 described in FIG. 1 and communicatively coupled to the radiation nozzle 200 described above with respect to FIG. 2. Alternately, computing system 600 may also be located externally with respect to the treatment room or suite containing treatment device 100 described in FIG. 1 and communicatively coupled to the radiation nozzle 200 described above with respect to FIG. 2.

By utilizing the systems and methods described above, the application of irradiated particles (such as protons) can be more accurately applied to a radiation subject with greater precision by efficiently and effectively modifying beam characteristics through a beam limiting structure, thereby shielding areas of a radiation subject outside the target area without the need for patient-customized apertures and complex multi-leaf collimator arrangements. This modification—all of which can be performed within a control system executing in a single, computing system—can effectively reduce radiation from beam applications from being received in unintended and untargeted areas, and provide a more accurate application of radiation plans for radiation subjects.

Although the subject matter has been described in language specific to structural features and/or processological acts, it is to be understood that the subject matter defined in the appended claims is not necessarily limited to the specific features or acts described above. Rather, the specific features and acts described above are disclosed as example forms of implementing the claims.

What is claimed is:

1. A proton beam emitting device comprising:
   a radiation nozzle configured to receive a beam of protons generated at a radiation source and to direct the beam of protons at a target area in an application subject;
   a planar beam limiting structure disposed in the radiation nozzle and configured to be positioned to modify the beam of protons by at least partially obstructing a path of the beam of protons to prevent irradiated particles from the beam of protons from being received in an area of the application subject outside of the target area, wherein the planar beam limiting structure comprises a single continuous and nonlinear structure that has surfaces facing each other; and
   a control system disposed in the radiation nozzle and configured to control a position of the planar beam limiting structure based on a position of the target area.

2. The device according to claim 1, wherein the beam of protons comprises a spot-scanning proton beam, and further wherein the spot-scanning proton beam is applied to the target area as a plurality of spots scanned over the target area as a raster scan.

3. The device according to claim 1, wherein the radiation nozzle is configured to be re-positioned around the application subject.

4. The device according to claim 1, where the planar beam limiting structure is configured to be re-positioned in the path of the beam of protons.

5. The device according to claim 1, wherein the radiation nozzle is coupled to a gantry, the gantry being configured to variably position the radiation nozzle around the application subject.

6. The device according to claim 1, wherein at least a portion of the planar beam limiting structure comprises a radiation shielding material.

7. The device according to claim 1, wherein a perimeter of the planar beam limiting structure at least substantially encloses an aperture.

8. The device according to claim 1, wherein the planar beam limiting structure comprises:
a first portion comprising a radiation shielding material; and
a second portion comprising a non-radiation shielding material,
wherein the control system is configured to control a position of the planar beam limiting structure so that the first portion of the planar beam limiting structure at least partially obstructs the path of the beam based on the position of the target area.

9. The device according to claim 1, wherein the planar beam limiting structure comprises at least one shape selected from the group consisting of:
a ring shape; and
a spiral shape.

10. The device according to claim 1, wherein the radiation source is configured to generate the beam of protons at a plurality of varying energies, and
further wherein at least one of a shape and a size of the planar beam limiting structure is customized for a first energy of the plurality of varying energies.

11. The device according to claim 1, further comprising a plurality of motors coupled to the planar beam limiting structure and controlled by the control system,
wherein the plurality of motors is configured to position the planar beam limiting structure via movement and rotation of the planar beam limiting structure in at least two dimensions.

12. The device according to claim 11, wherein the device comprises a single motor for each dimension of the at least two dimensions.

13. The device according to claim 1, wherein the control system is operable to position the planar beam limiting structure to limit an application of the beam of protons to a spot application from any direction.

14. The device according to claim 1, wherein the control system is configured to position the planar beam limiting structure to align with at least a portion of a border of the target area along a plane perpendicular to the beam axis.

15. The device according to claim 1, wherein the control system is configured to position the planar beam limiting structure to match a beam divergence of the beam of protons.

16. A system for producing beam-limited radiation applications, the system comprising:
a radiation source;
a beam line coupled to the radiation source and configured to transfer a beam of irradiated particles from the radiation source to at least one radiation application room;
a beam application device disposed in a radiation application room and configured to apply the beam of irradiated particles as a beam of protons to a target area, the beam application device comprising a rotating gantry and a radiation application nozzle;
a beam limiting device disposed in the radiation application nozzle, wherein the planar beam limiting structure comprises a single continuous and nonlinear structure that has surfaces facing each other;
a plurality of motors disposed in the radiation application nozzle, the plurality of motors being configured to collectively adjust a position of the beam limiting device in a plurality of dimensions;
a control system disposed in the beam application device, the control system being configured to control the plurality of motors to position the beam limiting device based on a target application of the beam of protons; and
a snout disposed on an end of the radiation nozzle and configured to emit the beam of irradiated particles.

17. The system according to claim 16, wherein the beam limiting device comprises:
a first portion comprising a radiation shielding material; and
a second portion comprising a non-radiation shielding material.

18. The system according to claim 17, wherein the control system is configured to position the beam limiting device to align with at least a portion of a border of the target area along a plane perpendicular to a beam axis.

19. The system according to claim 17, wherein the control system is configured to position the beam limiting device to match a beam divergence of the beam of irradiated particles.

20. A method for limiting a proton beam, the method comprising:
receiving, in a radiation nozzle, a beam of protons generated at a radiation source coupled to the radiation nozzle;
determining, in a control system disposed in the radiation nozzle, a position of a target area in an application subject;
positioning, via a plurality of motors communicatively coupled to the control system, a planar beam limiting structure to at least partially obstruct a path of the beam of protons to prevent radiation from the beam of protons from being received in an area of the application subject outside the target area, wherein the planar beam limiting structure comprises a single continuous and nonlinear structure that has surfaces facing each other; and
directing the beam of protons to the target area,
wherein the planar beam limiting structure is positioned to align with at least a portion of a border of the target area along a plane perpendicular to a beam axis.

* * * * *